(12) United States Patent
Suzuki

(10) Patent No.: US 8,562,514 B2
(45) Date of Patent: Oct. 22, 2013

(54) MEDICAL APPARATUS AND ENDOSCOPE SYSTEM WITH MEMORY FUNCTION

(75) Inventor: Akira Suzuki, Uenohara (JP)

(73) Assignee: Olympus Medical Systems Corp. (JP)

( * ) Notice: Subject to any disclaimer, the term of this patent is extended or adjusted under 35 U.S.C. 154(b) by 727 days.

(21) Appl. No.: 12/685,051

(22) Filed: Jan. 11, 2010

(65) Prior Publication Data

US 2010/0113877 A1    May 6, 2010

Related U.S. Application Data

(63) Continuation of application No. PCT/JP2007/063921, filed on Jul. 12, 2007.

(51) Int. Cl.
*A61B 1/00* (2006.01)
(52) U.S. Cl.
USPC .......................................... 600/117
(58) Field of Classification Search
USPC .......................................... 600/117
See application file for complete search history.

(56) References Cited

U.S. PATENT DOCUMENTS

| 4,402,311 | A  | * | 9/1983  | Hattori ........................... 600/117 |
| 4,409,993 | A  | * | 10/1983 | Furihata ......................... 607/116 |
| 6,981,941 | B2 | * | 1/2006  | Whitman et al. ................. 600/1 |
| 2007/0149857 | A1 | * | 6/2007 | Yabe et al. ..................... 600/180 |
| 2007/0219413 | A1 | * | 9/2007 | Lin ............................... 600/160 |
| 2008/0177141 | A1 | * | 7/2008 | Wu et al. ....................... 600/112 |
| 2009/0203965 | A1 | * | 8/2009 | Fujiyama et al. ............. 600/130 |
| 2010/0097454 | A1 | * | 4/2010 | Kubo et al. .................... 348/65 |
| 2010/0137682 | A1 | * | 6/2010 | Doguchi et al. .............. 600/109 |
| 2010/0145146 | A1 | * | 6/2010 | Melder .......................... 600/112 |
| 2011/0184239 | A1 | * | 7/2011 | Wright et al. .................. 600/118 |
| 2012/0197082 | A1 | * | 8/2012 | Uchiyama et al. ............ 600/114 |

FOREIGN PATENT DOCUMENTS

JP    2004-212240    7/2004
JP    2007-050108    3/2007

OTHER PUBLICATIONS

International Search Report and Written Opinion mailed Aug. 14, 2007 in corresponding PCT International Application No. PCT/JP2007/063921.
Notification of Transmittal of Translation of the International Preliminary Report on Patentability (IPRP) issued by the IPEA/EP Patent Office dated Feb. 25, 2010 (6 pages).

* cited by examiner

*Primary Examiner* — Rodney Fuller
*Assistant Examiner* — Linda B Smith
(74) *Attorney, Agent, or Firm* — Ostrolenk Faber LLP

(57) ABSTRACT

A medical apparatus having a medical device that is utilized to perform a predetermined medical action, includes an energy supply source including an attachment/detachment portion to/from which the medical device is attached/detached, and supplies energy when the medical device is utilized to perform the predetermined medical action, an energy output adjustment unit which adjusts the energy supplied from the energy supply source to medical action energy suitable for performing the predetermined medical action by using the medical device when the medical device is connected to the attachment/detachment portion, and an energy supply detecting mechanism for detecting a state that the energy supply source has supplied the medical action energy. When the determination mechanism detects a state that the energy supply source has supplied the medical action energy, the energy output from the energy supply source is prevented from being supplied to the medical device.

1 Claim, 4 Drawing Sheets

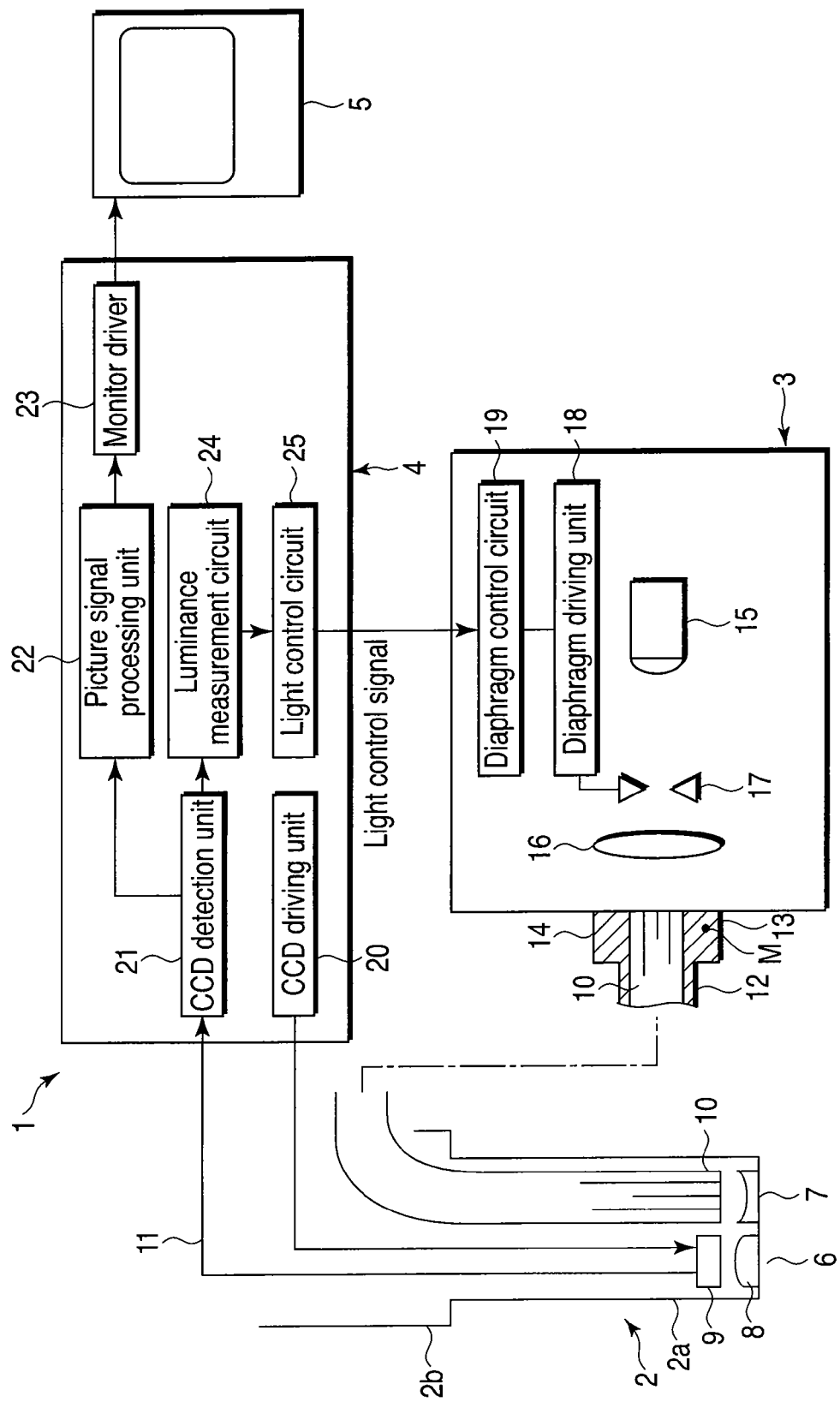
F I G. 1

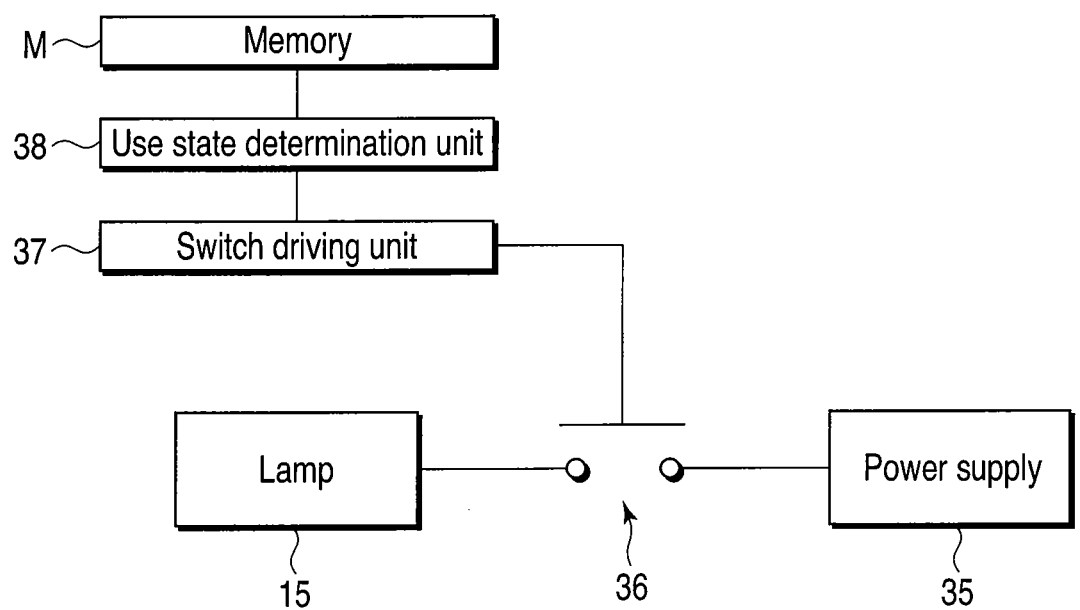
F I G. 3

MEDICAL APPARATUS AND ENDOSCOPE SYSTEM WITH MEMORY FUNCTION

CROSS-REFERENCE TO RELATED APPLICATIONS

This is a Continuation Application of PCT Application No. PCT/JP2007/063921, filed Jul. 12, 2007, which was published under PCT Article 21(2) in Japanese.

BACKGROUND OF THE INVENTION

1. Field of the Invention

The present invention relates to a disposable medical apparatus wherein a once-utilized device is discarded without being reused.

2. Description of the Related Art

As a medical device in conventional examples, there is a disposable medical device that is discarded without being reused when it is utilized once. As this disposable medical device, there is, e.g., a disposable endoscopic system disclosed in, e.g., JP-A 2007-050108 (KOKAI) (Patent Document 1). The disposable endoscope as a disposable medical device (which will be referred to as a disposable endoscope hereinafter) has a merit that it can be readily utilized for infected persons and others since it is disposable. However, the once-utilized disposable endoscope is reused if whether it has been used cannot be easily recognized, and using the disposable endoscope under unexpected circumstances can be anticipated.

Thus, in the apparatus disclosed in Patent Document 1, a memory that stores a used state is provided in the disposable endoscope. When a processor confirms contents in the memory upon connecting the disposable endoscope to the processor, an unused state or a used state is detected. Further, data concerning a use status is read from the memory to determine whether the disposable endoscope has been utilized. When it is determined that the disposable endoscope has been utilized, outputting a picture signal is stopped so that the picture signal cannot be input to a monitor and a message indicating that the disposable endoscope has been utilized is displayed in the monitor. As a result, the utilized disposable endoscope can be prevented from being erroneously reused.

In the apparatus having the above-described configuration, an operating state of the endoscope is detected and, if a state that the endoscope has been operated is detected, this operating state is stored in the memory. Furthermore, when the processor confirms contents in the memory upon connecting the disposable endoscope to the processor, whether the disposable endoscope has been utilized is detected. Therefore, for example, when the disposable endoscope is irradiated with illumination light from a light source in a state where the disposable endoscope is connected with a light source device, the memory stores a state that the disposable endoscope has been utilized.

Usually, it is general to confirm an operation of the endoscope before it is actually used for a patient. A use preparatory work, e.g., confirming an operation of the endoscope is carried out at a bright place outside a human body. At the bright place, the light source usually outputs illumination light having a maximum light quantity.

On the other hand, when the endoscope is put into a human body, a surrounding area of an observation optical system becomes dark. At a dark place like this example, the light source automatically starts light control to reduce a light quantity. That is, at the time of ordinary use that the endoscope is utilized while being inserted in a lumen of a human body, a light quantity of illumination light emitted from the light source is controlled to a light quantity that is suitable for observing the inside of the lumen, for example. This can be also applied to the use of the disposable endoscope.

BRIEF SUMMARY OF THE INVENTION

According to one aspect of the invention, there is provided a medical apparatus having a medical device that is utilized to perform a predetermined medical action, comprising: an energy supply source including an attachment/detachment portion to/from which the medical device is attached/detached, and supplies energy when the medical device is utilized to perform a predetermined medical action; an energy output adjustment unit which adjusts the energy supplied from the energy supply source to medical action energy suitable for performing the predetermined medical action by using the medical device when the medical device is connected to the attachment/detachment portion; and an energy supply detecting mechanism for detecting a state that the energy supply source has supplied the medical action energy.

According to one other aspect of the invention, there is provided a medical apparatus comprising: an attachment/detachment portion to/from which a medical device utilized to perform a predetermined medical action is attached/detached; an energy supply source configured to supply energy suitable for performing the predetermined medical action by using the medical device connected with the attachment/detachment portion as medical action energy; a determination mechanism for determining whether the medical device connected with the attachment/detachment portion is the medical device to which the medical action energy has been already supplied; a storing mechanism for storing information determined by the determination mechanism; and an energy supply controlling mechanism for enabling a continuation of energy supply from the energy supply source only when the information stored in the storing mechanism is information indicative of the medical device to which the medical action energy has not been supplied.

According to one other aspect of the invention, there is provided a medical apparatus comprising: an attachment/detachment portion to/from which a medical device utilized to perform a predetermined medical action is attached/detached; an energy supply source configured to supply energy suitable for performing the predetermined medical action by using the medical device connected with the attachment/detachment portion as medical action energy; a determination mechanism for determining whether the medical device connected with the attachment/detachment portion is the medical device to which the medical action energy has been already supplied for a predetermined time; a storing mechanism for storing information determined by the determination mechanism; and an energy supply controlling mechanism for enabling a continuation of energy supply from the energy supply source only when the information stored in the storing mechanism is information indicative of the medical device to which the medical action energy has not been supplied for the predetermined time.

According to one other aspect of the invention, there is provided a medical apparatus comprising: an attachment/detachment portion to/from which a medical device utilized to perform a predetermined medical action is attached/detached; an energy supply source configured to supply energy to the medical device connected with the attachment/detachment portion; a determination mechanism for determining whether the medical device to which energy changed to medical action energy suitable for performing the predetermined medical action has been already supplied is connected with the attachment/detachment portion; a storing mechanism for storing information determined by the determination mechanism; and an energy supply controlling mechanism for enabling a continuation of energy supply from the energy supply source only when the information stored in the storing mechanism is information indicating that the medical device to which energy that has not been changed to the medical action energy has been supplied is connected with the attachment/detachment portion.

According to one other aspect of the invention, there is provided a medical apparatus comprising: an attachment/detachment portion to/from which a medical device is attached/detached; an energy supply source configured to supply energy to the medical device connected with the attachment/detachment portion; a determination mechanism for determining whether the medical device connected with the attachment/detachment portion is a medical device to which the energy has been already supplied for a predetermined time; a storing mechanism for storing information determined by the determination mechanism; and an energy supply controlling mechanism for enabling the continuation of energy supply from the energy supply source only when the information stored in the storing mechanism is information indicative of the medical device to which the energy has not been supplied for the predetermined time.

BRIEF DESCRIPTION OF THE SEVERAL VIEWS OF THE DRAWING

FIG. 1 is a schematic block diagram of an entire endoscopic system according to a first embodiment of the present invention;

FIG. 3 is a schematic block diagram for explaining a control circuit for a lamp switch according to the first embodiment.

DETAILED DESCRIPTION OF THE INVENTION

Figure 2:
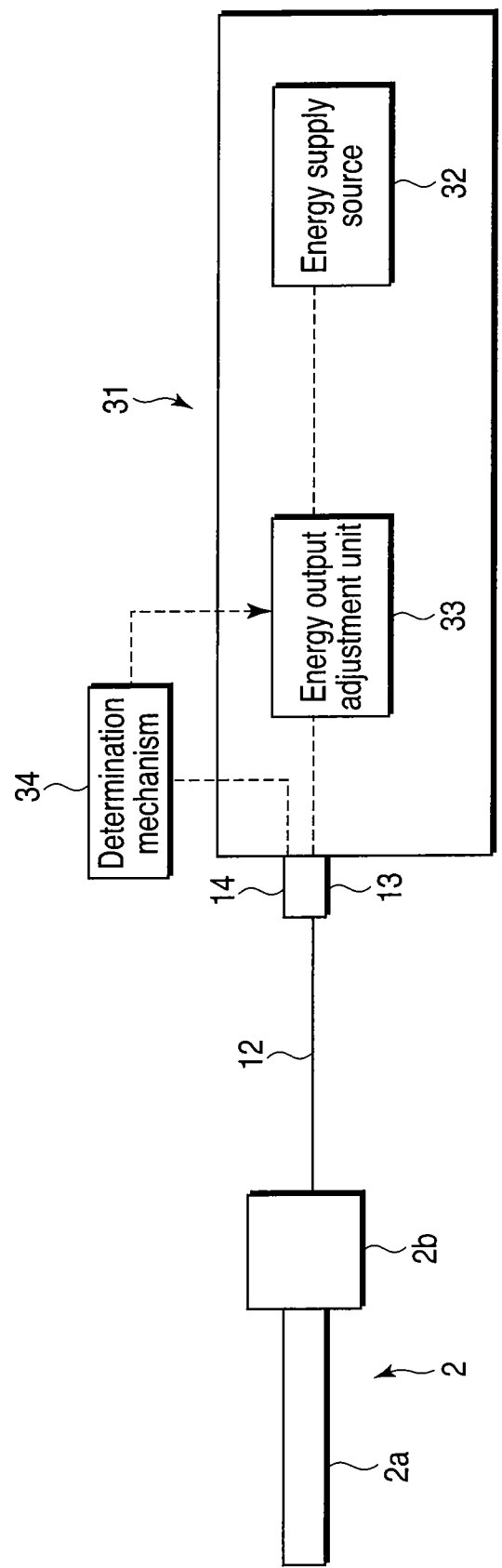
FIG. 2 is a schematic block diagram for explaining a control circuit for an endoscope according to the first embodiment.

A first embodiment according to the present invention will now be described hereinafter with reference to FIGS. 1 to 4. FIG. 1 is a schematic block diagram of an entire endoscopic system 1 as a medical apparatus according to the first embodiment of the present invention. The endoscopic system 1 is constituted of an endoscope (a medical device) 2 and peripheral devices thereof. The peripheral devices have a light source device 3 that generates illumination light for the endoscope, a display video processor (a camera control unit) 4 as an image processing device that executes various types of image processing with respect to image data acquired by an imaging unit in the endoscope 2, and a monitor 5 as a display device.

The endoscope 2 has an elongated inserting portion 2a that is inserted into a body and a front-side end portion 2b coupled with a proximal end of this inserting portion 2a. A distal end face of the inserting portion 2a has, e.g., one observation window portion 6, one illumination window portion 7, a non-illustrated opening portion of a treatment tool insertion channel, and others. On the inner side of the observation window portion 6, an imaging unit including an optical system such as an object lens 8 and an imaging element 9 such as a CCD is arranged. On the inner side of the illumination window portion 7, a distal end portion of a light guide fiber 10 is oppositely arranged. The light guide fiber 10, a cable 11 such as a signal wire for the imaging element 9, the non-illustrated treatment tool insertion channel, and others are extended to the front-side end portion 2b through the inside of the inserting portion 2a.

The front-side end portion 2b is coupled with one end of a universal cord 12. The light guide fiber 10 or the cable 11, e.g., the signal wire for the imaging element 9 is extended through the inside of the universal cord 12.

A connector portion 13 is coupled with the other end of the universal cord 12. A proximal end portion of the light guide fiber 10 is fixed at an end face position of the connector portion 13. The connector portion 13 is detachably coupled with a connector receiving portion (an attachment/detachment portion) 14 of the light source device 3.

Moreover, the connector portion 13 is connected with one end of a non-illustrated electrical cord. The cable 11, e.g., the signal wire for the imaging element 9 is extended through the inside of the electrical cord from the inside of the universal cord 12. The other end of the electrical cord is connected with the video processor 4 through a non-illustrated electrical connector.

Additionally, the light source device 3 has a lamp (an energy supply source) 15, a condenser lens 16, a diaphragm 17, a diaphragm driving unit 18, and a diaphragm control circuit 19. The lamp 15 is arranged at a position where it distantly faces the connector portion 13 connected with the connector receiving portion 14. The condenser lens 16 is arranged at a position where it condenses the illumination light emitted from the lamp 15 onto the proximal end portion of the light guide fiber 10 fixed at the connector portion 13. The diaphragm 17 is interposed between the lamp 15 and the condenser lens 16.

The diaphragm 17 is driven by the diaphragm driving unit 18. Further, the diaphragm driving unit 18 is connected with the diaphragm control circuit 19. Furthermore, the diaphragm control circuit 19 controls the diaphragm driving unit 18. As a result, when the operation of the diaphragm 17 is controlled, a light quantity of the illumination light emitted from the lamp 15 is adjusted.

Moreover, the video processor 4 has a CCD driving unit 20, a CCD detection unit 21, a picture signal processing unit 22, a monitor driver 23, a luminance measurement circuit 24, and a light control circuit 25. A driving signal output from the CCD driving unit 20 is input to a non-illustrated connection circuit substrate of the imaging element 9, thereby driving the imaging element 9. An imaging signal output from the imaging element 9 is input to the CCD detection unit 21 of the video processor 4.

The CCD detection unit 21 outputs two signals. One output signal output from the CCD detection unit 21 is transmitted to the monitor driver 23 through the picture signal processing unit 22. As a result, an imaging signal acquired by the imaging element 9 is supplied to the picture signal processing unit 22 from the CCD detection unit 21. The imaging signal from the imaging element 9 is converted into the picture signal in the picture signal processing unit 22, and this picture signal is supplied to the monitor 5 through the monitor driver 23. Consequently, an image acquired by the endoscope 2 is displayed in the monitor 5.

Moreover, the other output signal output from the CCD detection unit 21 is input to the luminance measurement circuit 24 to measure luminance. An output signal from this luminance measurement circuit 24 is supplied to the light control circuit 25. The light control circuit 25 is connected with the diaphragm control circuit 19. As a result, a light control signal output from the light control circuit 25 is adjusted in accordance with a measurement result obtained from measurement performed by the luminance measurement circuit 24. Consequently, when the light control signal transmitted from the light control circuit 25 to the diaphragm control circuit 19 is adjusted in accordance with the luminance of a picture obtained by the imaging element 9, the operation of the diaphragm 17 of the light source device 3 is controlled in accordance with the luminance of the picture, thereby adjusting a light quantity of the illumination light emitted from the lamp 15. At this time, information of an operating state (a light control state) of the light control circuit 25 is stored in, e.g., a built-in memory M in the connector portion 13 of the endoscope 2.

FIG. 2 is a schematic block diagram for explaining the control circuit 31 of the endoscope 2. The control circuit 31 includes an energy supply source 32, an energy output adjustment unit 33, and determination mechanism (energy supply detecting mechanism) 34. The energy supply source 32 has the connector receiving portion 14 to/from which the endoscope 2 can be attached/detached, and it supplies energy when taking a predetermined medical action by using the endoscope 2. In this embodiment, the energy supply source 32 corresponds to the lamp 15 of the light source device 3 depicted in FIG. 1.

When the connector portion 13 of the endoscope 2 is connected with the connector receiving portion 14, the energy output adjustment unit 33 adjusts (controls) a light quantity of the illumination light as energy output from the lamp 15 of the energy supply source 32 to medical action energy suitable for taking a predetermined medical action by using the endoscope 2, i.e., an adequate light quantity of the illumination light. In this embodiment, the energy output adjustment unit 33 corresponds to the diaphragm 17, the diaphragm driving unit 18, and the diaphragm control circuit 19 in FIG. 1.

The determination mechanism 34 detects a state that the energy supply source 32 has supplied the medical action energy, i.e., a state that the illumination light has been adjusted to have an adequate light quantity. In this embodiment, the determination mechanism 34 corresponds to a later-described use state determination unit 38.

As shown in FIG. 3, in the light source device 3 according to this embodiment, a lamp switch 36 is interposed between the lamp 15 and a power supply 35. A switch driving unit 37 is connected with the lamp switch 36. The use state determination unit 38 that determines a use state of the endoscope 2 connected with the light source device 3 is connected to the switch driving unit 37. When the connector portion 13 of the endoscope 2 is connected to the connector receiving portion 14, the use state determination unit 38 is connected with the built-in memory M in the connector portion 13 of the endoscope 2. The use state determination unit 38 determines a state of the endoscope 2 as a used state that the endoscope 2 has been actually utilized for a patient or an unused state that the endoscope 2 has not been actually utilized for the patient in accordance with information stored in the memory M of the endoscope 2.

It is to be noted that the illumination light emitted from the lamp 15 of the light source device 3 has been exemplified as the medical action energy in this embodiment, but energy suitable for taking a predetermined medical action by using a medical device, e.g., the endoscope 2 can suffice as this medical action energy. As the medical action energy different from the illumination light, for example, motive energy such as electric power, air, a water pressure, or an oil pressure can be adopted.

A function of the configuration will now be described. In the endoscopic system 1 according to this embodiment, operations of the endoscope 2 are confirmed before the endoscope 2 is actually utilized for a patient. A use preparatory work, e.g., the operation confirmation for the endoscope 2 is carried out at a bright place outside a human body. Further, the connector portion 13 of the endoscope 2 is connected with the connector receiving portion 14 of the light source device 3. In this state, the endoscope 2 is irradiated with the illumination light from the lamp 15 of the light source device 3. At this time, the diaphragm 17 of the light source device 3 is held in a fully opened state. Therefore, the illumination light emitted from the lamp 15 of the light source device 3 is led to the endoscope 2 without being stopped down, and hence the illumination light having a maximum light quantity is output.

At the time of the use preparatory work, e.g., the operation confirmation for the endoscope 2, the imaging element 9 is driven by a driving signal from the CCD driving unit 20. Furthermore, an imaging signal output from the imaging element 9 is input to the CCD detection unit 21 of the video processor 4, thus measuring luminance by the luminance measurement circuit 24. When a state where the illumination light having the maximum light quantity has been output from the light source device 3 is detected, the operation confirmation for the endoscope 2 is terminated. Here, when the light source device 3 is emitting the illumination light having the maximum light quantity, the use state determination unit 38 does not determine that the endoscope 2 is currently utilized but determines that it is utilized upon start of light control. Therefore, the endoscope 2 that has been subjected to the operation confirmation alone is not determined as in the used state.

Furthermore, when the endoscopic system 1 according to this embodiment is actually utilized for a patient, the endoscope 2 is inserted into a dark position, e.g., a body of the patient. At such a dark position, when the imaging signal output from the imaging element 9 is input to the CCD detection unit 21 of the video processor 4, the luminance measurement circuit 24 measures luminance, thereby detecting a state that the endoscope 2 has been put in the dark position, e.g., the inside of the body. Therefore, in this case, a light control signal output from the light control circuit 25 is adjusted in accordance with a result of the measurement carried out by the luminance measurement circuit 24. As a result, the light control signal transmitted from the light control circuit 25 to the diaphragm control circuit 19 is adjusted in accordance with the luminance of a picture obtained by the imaging element 9 to control an operation of the diaphragm 17 of the light source device 3 in accordance with the luminance of the picture, thereby adjusting a light quantity of the illumination light emitted from the lamp 15. At this time, information of an operating state (a light control state) of the light control circuit 25 is stored in the built-in memory M in the connector portion 13 of the endoscope 2.

Figure 4:
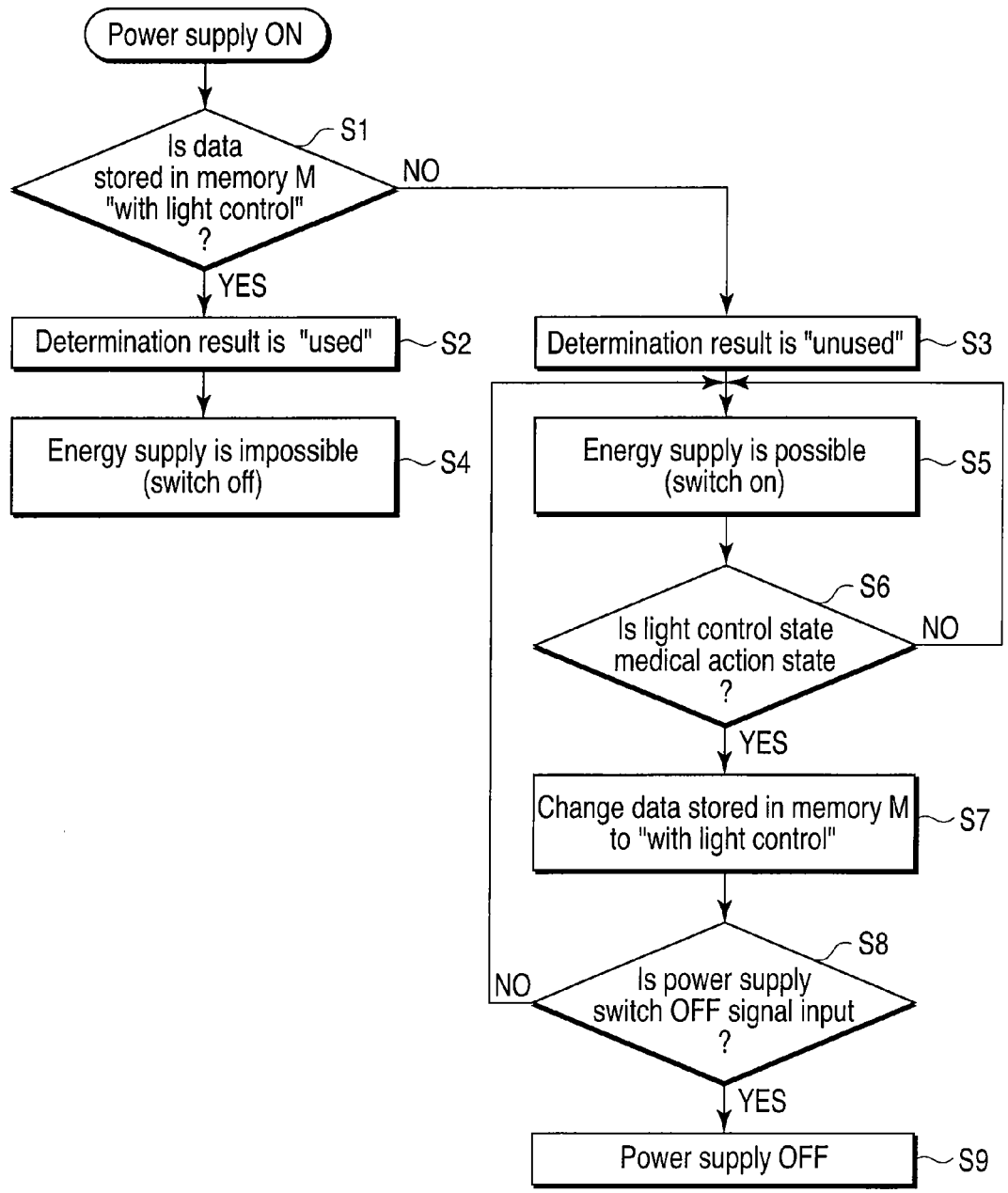
FIG. 4 is a flowchart for explaining an operation of a use state determination unit on the endoscope according to the first embodiment.

Moreover, in the endoscopic system 1 according to this embodiment, when the connector portion 13 of the endoscope 2 is connected with the connector receiving portion 14 of the light source device 3, the use state determination unit 38 is connected with the built-in memory M in the connector portion 13 of the endoscope 2. Additionally, the use state determination unit 38 determines a use state of the endoscope 2 connected with the light source device 3. FIG. 4 is a flowchart for explaining an operation of the use state determination unit 38 at this moment. When the use state determination unit 38 operates, data stored in the memory M is first read out, and whether the data stored in the memory M is "with light control" is determined (a step S1).

When it is determined that the data is "with light control" at this step S1, the processing advances to a subsequent step S2. At this step S2, the endoscope 2 is determined as being used. Further, when it is determined that the data is "without light control" at step S1, the processing proceeds to a subsequent step S3. At this step S3, the endoscope 2 is determined as being unused.

When the endoscope 2 is determined as being used at step S2, a control signal which is utilized to turn off the lamp switch 36 is supplied to the switch driving unit 37 from the use state determination unit 38 at a subsequent step S4. As a result, the lamp switch 36 is held in the OFF state by the switch driving unit 37. Therefore, the lamp 15 is not turned on, and hence the endoscope 2 connected with the light source device 3 is held in an unusable state.

Furthermore, when the endoscope 2 is determined as being unused at step S3, a control signal which is utilized to turn on the lamp switch 36 is supplied to the switch driving unit 37 from the use state determination unit 38. As a result, the switch driving unit 37 switches the lamp switch 36 to the ON state. Therefore, the endoscope 2 connected with the light source device 3 is changed over to a usable state.

Thereafter, at a subsequent step S6, whether the light control state is a medical action state or any other state (a use preparatory work such as operation confirmation) is determined.

When the light control state is determined as the medical action state at this step S6, the processing advances to a subsequent step S7. At this step S7, the data stored in the memory M is changed to "with light control". Further, when the light control state is determined as a state other than the medical action state at step S6, the processing returns to the operation before step S5.

Furthermore, after step S7, whether an input signal which is utilized to turn off the power supply switch has been input by an operator is determined at a subsequent step S8. It is to be noted that, when the input signal which is utilized to turn off the power supply switch has not been input at step S8, the processing advances to a subsequent step S9 to turn off the power supply. When it is determined that the input signal which is utilized to turn off the power supply switch has not been input at step S8, the processing returns to the operation before step S5.

Thus, the above-described configuration demonstrates the following effect. That is, in the endoscopic system 1 according to this embodiment, when the connector portion 13 of the endoscope 2 is connected with the connector receiving portion 14 of the light source device 3, the data stored in the built-in memory M in the connector portion 13 of the endoscope 2 is read out by the use state determination unit 38, and a use state of the endoscope 2 connected with the light source device 3 is determined by the use state determination unit 38 based on the data stored in the memory M. Moreover, when the use state determination unit 38 determines that the endoscope 2 is in the used state, the switch driving unit 37 maintains the lamp switch 36 in the OFF state. As a result, when the used endoscope 2 is connected with the light source device 3, the lamp 15 of the light source device 3 is not turned on, and an unusable state is held. Therefore, the used disposable endoscope 2 can be prevented from being reused.

Additionally, when the light source device 3 emits the illumination light having a maximum light quantity, the use state determination unit 38 does not determine that the endoscope 2 is in use but determines that it is in use upon start of light control. Therefore, since the endoscope 2 which has been subjected to the operation confirmation alone is not determined as being used, the endoscope 2 connected with the light source device 3 is switched to the usable state. Therefore, in the endoscopic system 1 according to this embodiment, before use of the disposable endoscope 2, the fact that this endoscope 2 has been actually utilized for an actual medical action rather than a test, e.g., use preparation can be supplied to the medical device as appropriate information. As a result, the endoscope 2 which has been subjected to the operation confirmation but not utilized for a patient can be prevented from being discarded as a used endoscope.

Further, the present invention is not restricted to the foregoing embodiment. For example, the use state determination unit 38 may be configured to have a timer function for detecting whether the illumination light controlled to have an adequate light quantity for the illumination light has been supplied to the endoscope 2 for a preset time. In this case, when a time for which the controlled illumination light is supplied to the endoscope 2 exceeds the preset time, the use state determination unit 38 determines that the endoscope 2 is in the used state. Furthermore, when a time for which the controlled illumination light is supplied to the endoscope 2 does not reach the preset time, the use state determination unit 38 determines that the endoscope 2 is in the unused state.

When the time for which the controlled illumination light is supplied to the endoscope 2 exceeds the preset time, the use state determination unit 38 according to this modification determines that the endoscope 2 is in the used state. Therefore, the endoscopic system 1 according to this modification can prevent the endoscope 2 from being determined as being used even when the time for which the controlled illumination light is supplied to the endoscope 2 does not reach the preset time. Accordingly, before the disposable endoscope 2 is used, the fact that this endoscope 2 has been utilized for an actual medical action rather than a test such as use preparation can be supplied to the medical device as more appropriate information.

Moreover, the foregoing embodiment has disclosed the configuration that the diaphragm 17, the diaphragm driving unit 18, and the diaphragm control circuit 19 are provided in the light source device 3 and the diaphragm 17 adjusts an opening area of the opening portion through which the illumination light is led to, thereby adjusting a light quantity of the illumination light. This may be substituted by a configuration that a dedicated lamp that is used for a use preparation work, e.g., operation confirmation and a light control lamp are separately provided and these two lamps are separately utilized.

Additionally, in each embodiment, it is possible to provide notifying mechanism for notifying (warning) the fact that the endoscope (the medical device) that has been utilized for an actual medical action is attached to the medical apparatus.

Further, besides, the present invention can be of course modified in many ways without departing from the scope of the invention.

The present invention is effective in a technical field for manufacturing and using a medical apparatus having a disposable medical device that is discarded without being reused when it is once utilized.

What is claimed is:

1. An endoscopic system including an endoscope configured to be inserted into a body cavity, the endoscopic system comprising:
a light source device configured to emit an illumination light;
a light guide fiber which is arranged to the endoscope, and which is configured to receive the illumination light;
a connector arranged at a proximal end portion of the light guide fiber;

a receiving connector which is detachably coupled with the connector, and which is configured to bring the illumination light, emitted from the light source device, to the light guide fiber;

a memory which is arranged in the endoscope, and which is configured to store information of indicating whether or not the endoscope has been inserted into a body cavity;

a use state determination unit configured to read out the information, and configured to determine a use state as a used state in which the endoscope has been inserted into the body cavity or as an unused state in which the endoscope has not been inserted into the body cavity, in accordance with the information when the connector is connected with the receiving connector;

a switch driving unit configured to cause the light source device to emit the illumination light into the light guide fiber only when the use state determination unit determines the use state as the unused state;

a light controller configured to adjust a light quantity of the illumination light emitted from the light source device;

an imaging element which is arranged to the endoscope, and which is configured to obtain pictures; and a luminance measurement apparatus configured to measure luminance of the pictures obtained by the imaging element, wherein the use state determination unit is configured to determine the use state stored in the memory in accordance with a light control state of the light controller, the use state determination unit is configured to determine the use state as the used state only when the light controller has controlled the light quantity of the illumination light, the light controller is configured to control the light quantity of the illumination light when the luminance measurement apparatus detects a state in which the endoscope has been put in a dark position, in accordance with the luminance measured by the luminance measurement apparatus, and the use state stored in the memory is configured to be changed to the used state when the light controller controls the light quantity of the illumination light.

* * * * *